United States Patent [19]
Eigler

[11] Patent Number: 5,144,148
[45] Date of Patent: * Sep. 1, 1992

[54] PROCESS FOR REPOSITIONING ATOMS ON A SURFACE USING A SCANNING TUNNELING MICROSCOPE

[75] Inventor: Donald M. Eigler, Santa Cruz, Calif.

[73] Assignee: International Business Machines Corporation, Armonk, N.Y.

[*] Notice: The portion of the term of this patent subsequent to Jan. 22, 2008 has been disclaimed.

[21] Appl. No.: 569,270

[22] Filed: Aug. 17, 1990

Related U.S. Application Data

[63] Continuation-in-part of Ser. No. 432,657, Nov. 7, 1989, Pat. No. 4,987,312.

[51] Int. Cl.$^5$ .............................................. H01J 37/30
[52] U.S. Cl. .............................. 250/492.3; 250/492.2; 369/101; 369/126
[58] Field of Search .......................... 250/492.3, 492.2; 369/101, 126

[56] References Cited

U.S. PATENT DOCUMENTS

| | | | |
|---|---|---|---|
| 4,575,822 | 3/1986 | Quate | 365/174 |
| 4,826,732 | 5/1989 | Kazan et al. | 428/432 |
| 4,945,515 | 7/1990 | Ooumi et al. | 369/126 |
| 4,987,312 | 1/1991 | Eigler | 250/492.3 |

OTHER PUBLICATIONS

Gomer, IBM Journal of Research and Development, vol. 30, No. 4, Jul. 1986, pp. 428-430.

Primary Examiner—Jack I. Berman
Attorney, Agent, or Firm—Henry E. Otto, Jr.

[57] ABSTRACT

A method and structure in which an adsorbate atom or molecule is repositioned on a substrate surface by moving the tip of an STM to a position adjacent to the atom to be moved and causing the atom to be attracted to the tip. While the atom remains bound to the surface (or, alternatively, is lifted), the tip is moved laterally to drag (or carry) the atom to a desired position at which it is bound to the surface.

The atom may be repositioned in close proximity to an atom of the same or another type on the same or a different substrate to create a desired multi-atom structure or synthesize a molecule, or an atom may be removed to cleave a multi-atom structure, or a change in state of a multi-atom structure may be effected.

Atoms may also be repositioned to write indicia on a storage medium by dragging or carrying atoms into the desired information-bearing pattern, for example, by dragging or carrying selected atoms out of a respective one of a plurality of parallel atom rows using the tip of an STM to thereby write indicia at locations denoted by the removed atoms.

26 Claims, 2 Drawing Sheets

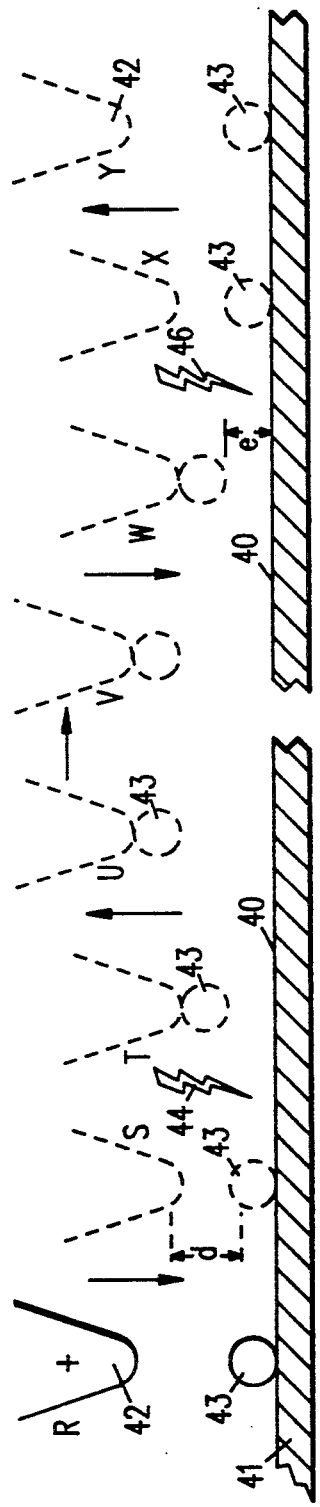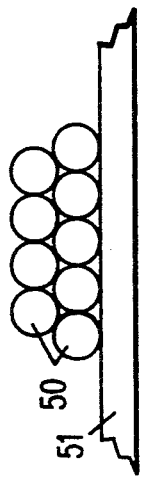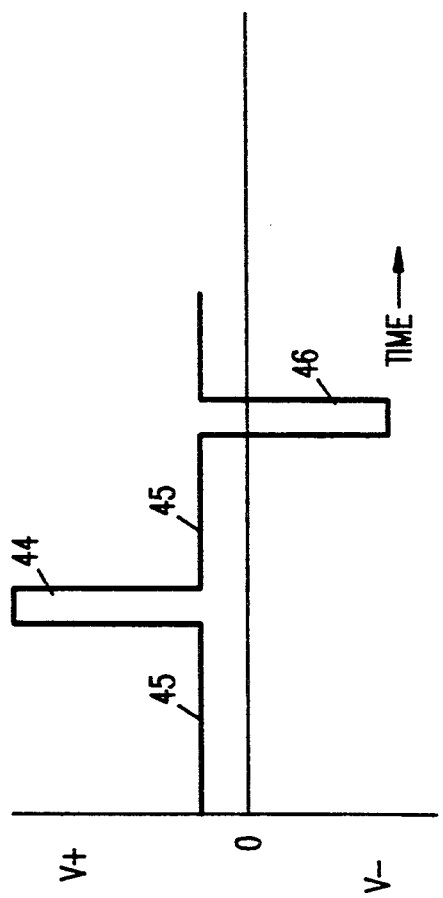

PROCESS FOR REPOSITIONING ATOMS ON A SURFACE USING A SCANNING TUNNELING MICROSCOPE

CROSS REFERENCE TO RELATED APPLICATION

This is a continuation-in-part of copending application Ser. No. 07/432,657, filed Nov. 7, 1989, now U.S. Pat. No. 4,987,312, granted Jan. 22, 1991.

FIELD OF THE INVENTION

This invention relates to methods and structures involving repositioning of atoms or molecules adsorbed on a substrate and, more particularly, to a method using a scanning tunneling microscope (STM) for repositioning an atom or molecule on a substrate (such as for fabricating or disassembling a multi-atom structure, synthesizing or cleaving a multi-atom structure, or recording indicia on a storage medium) and the products made by said method.

BACKGROUND OF THE INVENTION

U.S. Pat. No. 4,575,822 to Quate describes a data storage medium on which, using an STM with a probe tip, indicia are written by forming perturbations on the surface of a substrate. The indicia are then read by scanning over the indicia with the tip of the STM.

The most pertinent prior art of which applicant is aware is U.S. Pat. No. 4,826,732 to Kazan, which also describes several embodiments of a recording medium. One comprises a substrate having a surface coated with a monolayer of atoms and from which atoms are selectively removed by modulating the input signal to an STM tip to write indicia. Another embodiment comprises a substrate having a surface onto which atoms are selectively deposited to write indicia. In both embodiments, the STM is used to read back information by imaging the surface.

An article by Becker et al. entitled "Atomic-scale Surface Modifications Using a Tunneling Microscope", published in the Jan. 29, 1987, issue of Nature, pp. 419–421, describes writing an atomic-scale "bit" by raising the STM tip to substrate bias from $-1.0$ V to $-4.0$ V at a quiescent tunnel current of 20 pA while the tip is maintained laterally stationary over the site chosen for modification, then rapidly withdrawing the tip. However, this article does not teach repositioning an atom.

No prior art known to applicant discloses or suggests the repositioning of an atom or molecule from one position on the surface of a substrate to another position on said surface, or the repositioning of atoms or molecules of the same or different type on the same surface to fabricate a desired multi-atom structure, such as an electrical component, or to synthesize or cleave a multi-atom structure, such as a biological molecule (e.g., a protein or a nucleic acid), or a long-chain polymer.

SUMMARY OF THE INVENTION

A method is disclosed for repositioning an adsorbate atom (or molecule) on a substrate surface by moving the tip of an STM to a position adjacent to the atom to be moved and subsequently increasing the attraction between the tip and atom by moving the tip closer to the substrate; and then, while the atom remains bound to the surface, moving the tip laterally to drag the atom to a desired position on the surface. The tip is then moved away from the substrate, reducing the attraction between the atom and tip, and leaving the atom bound at the desired position.

The atom may be repositioned in close proximity to an atom of the same or another type on the substrate to create a desired multi-atom structure or synthesize or cleave a multi-atom structure.

Atoms may also be repositioned to write indicia on a storage medium by dragging atoms into the desired information bearing pattern, for example, by dragging selected atoms out of a respective one of a plurality of parallel atom rows using the tip of an STM to thereby write indicia at locations denoted by the removed atoms.

Atoms may also be repositioned by lowering the STM tip over the atom to be moved and changing the voltage/current until the atom becomes transferred to the tip; whereupon the voltage/current may be reduced or zeroed or, if preferred, maintained. The tip is retracted, moved laterally, and then lowered to reposition the atom on the same or another substrate; whereupon the voltage/current is changed to leave the atom substrate bound when the tip is retracted.

BRIEF DESCRIPTION OF THE DRAWINGS

FIG. 4 is a schematic view illustrating another preferred technique for repositioning an atom.

FIG. 5 is a plot of voltage v. time for the technique illustrated in FIG. 4.

FIG. 6 is a side elevational view of a multi-atom, three-dimensional structure fabricated by any of the methods embodying the invention.

DESCRIPTION OF PREFERRED EMBODIMENTS

For simplification of description, the term "atom" as herein used in the specification and claims is intended to define either an atom or a molecule, unless otherwise indicated. Also, since operation of an STM was initially described in U.S. Pat. No. 4,343,993 and is now well known in the art, its operation will be but briefly described herein.

I

Figure 1:
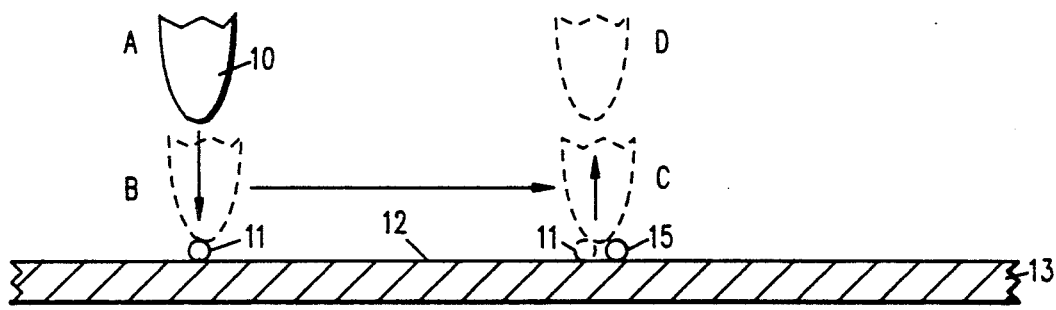
FIG. 1 is a schematic view showing a preferred technique for repositioning an atom on a surface.

One preferred method for repositioning "atoms" is illustrated in FIG. 1. A probe tip 10 of a scanning tunneling microscope (STM) is disposed above an adsorbate atom 11 that is bound to the surface 12 of an adsorbent substrate 13. A bias voltage and current of sufficiently low magnitude to prevent unintended movement of atom 11 is applied to tip 10 to initially locate and target the atom on surface 12 by using the STM in conventional imaging mode. Tip 10 is then moved from point A toward atom 11 (e.g., by increasing the tunnel current), until the tip is capable of exerting enough lateral force on the atom to cause the atom to remain located beneath the tip but bound to the substrate when the tip is subsequently moved laterally across the surface. Tip 10 is then moved laterally to point C (using a conventional STM feedback circuit, not shown, to maintain constant tunneling current), dragging the atom with it along a preselected path to the desired new position. Throughout this lateral movement, the atom remains bound to the surface. At the new position, the tip is withdrawn to position D, leaving the atom bound at the new position.

In a similar manner, while the top of an STM is positioned within an effective distance proximate a selectable group of atoms to be moved, a voltage may be applied between the tip and substrate to increase the attraction between the tip and one or more atoms of the group. Then, while the group of atoms remains bound to the surface, the tip is moved laterally to drag or otherwise shift a group of atoms to a desired position on the surface. Thereafter, while the tip is within the effective distance, a voltage pulse can be applied between the tip and substrate for causing the selected group of atoms to become repositioned on the surface. The selected group of atoms may be a three-dimensional cluster.

For proper operation, it is necessary to provide a combination of adsorbate atom and substrate surface which will assure that the energy barrier to move from position to position on the surface is smaller than the energy gained by having the atom remain in the region between the tip and substrate. The sign and magnitude of the electric field between the tip and the substrate may be used to change the attractive interaction between the atom and the tip to facilitate the process of dragging an atom across the surface.

In actual test, a Xe atom was dragged from one position to another on the surface of a Pt (111) substrate in the following manner with the atom and substrate disposed in an evacuated container and at a temperature of 4° K.

(1) The Xe atom was targeted and its x,y coordinates determined by imaging the surface using a tunnel current of $1 \times 10^{-11}$ amp. and a negative 0.020 voltage between the tip and substrate.

(2) The tip was then lowered toward the targeted Xe atom by increasing the demanded tunneling current to $2 \times 10^{-10}$ amp.

(3) The tip was then moved sequentially in x and then y directions to a new position whose x,y coordinates were preselected, dragging the Xe atom, which remained bound to the Pt surface, en route. This was done with the STM operating in constant current mode at $2 \times 10^{-10}$ amp.

(4) The tunnel current was then reduced to $1 \times 10^{-11}$ amp. (the imaging current) causing the tip to be retracted from the substrate. This effectively terminated the attraction between the Xe atom and the tip, leaving the atom bound to the surface at its new location when the tip was subsequently moved laterally.

While the described experiment was performed considerably below room temperature, the ability to successfully reposition an atom on a surface using this process is not fundamentally dependent upon temperature. In other words, the lateral (i.e., in-plane), attractive interaction between the atom and the tip must be sufficiently strong to overcome the energy barrier for an atom to move from site to site along the surface, and the attraction the atom has to the tip must not be so great as to cause the atom to become bound to the tip instead of remaining bound to the surface. Since the energy barrier for moving an atom from site to site across the surface is generally smaller than the atom's adsorption energy, this process will work for a wide range of adsorbate atoms/molecules adsorbed on a wide range of substrates.

This method may also be used to drag an atom up or down steps or over a substrate having an uneven surface by constraining the tip to follow changes in vertical contour.

II

Figure 2:
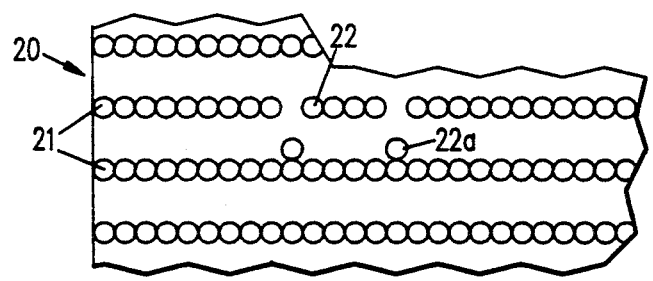
FIG. 2 is a fragmentary view of a recording medium on which data is written using one preferred technique.

The method may also be used to write indicia on a storage medium. As illustrated in FIG. 2, a storage medium 20 in the form of a substrate with an adsorbent surface is provided with a plurality of parallel rows 21 of atoms 22 of similar type, and the rows are spaced apart substantially one atom width.

To write indicia, a selectable atom 22a in a selected row is imaged and targeted as above described, and then dragged out of the row into the vacant space between rows while bound to the surface, then released by the tip. After a sequence of these writing steps, the indicia may be read by scanning either each row (or the spaces between rows) sequentially with the tip.

If a substrate with atoms row arranged is not available, atoms from a supply area of the substrate may be individually dragged and repositioned into rows using the method above described. Or, if preferred, the atoms may be expelled and deposited in a series of parallel rows by an adaptation of the technique described in connection with FIGS. 5 or 6 of the above-cited patent to Kazan.

III

Figure 3:
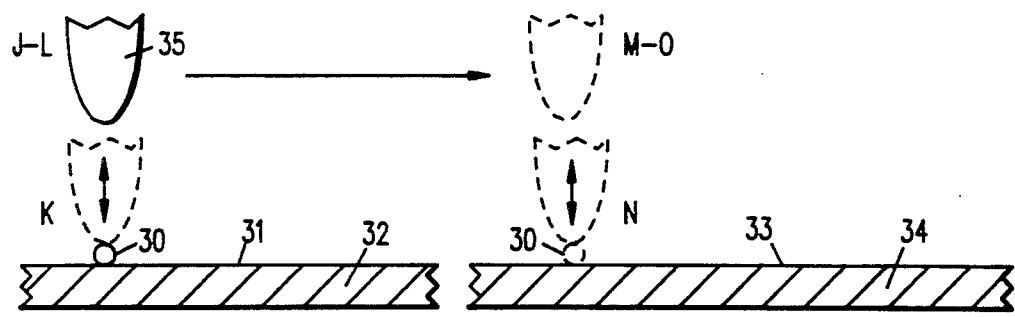
FIG. 3 is a schematic view of an alternative technique for repositioning an atom from one substrate to a different substrate.

FIG. 3 illustrates a method for repositioning a selected atom 30 from surface 31 of one substrate 32 to a surface 33 of another, or the same, substrate 34. STM tip 35 images and targets atom 30 at position J. The tip is then brought to position K such that atom 30 becomes bound to the tip. The tip, with atom attached, is retracted from substrate 32 to position L, then translated to position M above the preselected site at which the atom is to be deposited on surface 33 of substrate 34. The tip 35 is then lowered to position N, at which point atom 30 becomes bound to surface 33. The tip is then withdrawn to position 0, leaving the atom bound to the surface 33.

It will be understood that the applied bias voltage between the tip and substrate and the tunneling current may be adjusted so as to facilitate the transfer of the atom to the tip when the tip is at point K, and may also be adjusted to facilitate the transfer of the atom from the tip to the surface 33 when the tip is at point N.

IV

In actual test and as depicted in FIGS. 4 and 5, surface 40 of a Pt(111) substrate 41 was imaged with the tip 42 of an STM at a voltage 45 (FIG. 5) to locate the Xe atom 43 which was to be moved. Tip 42 was then lowered from its imaging position R to position S which is within a predetermined distance d from adsorbed atom 43. Then a voltage pulse 44 of appropriate magnitude, polarity, and duration was applied between the tip and substrate. In this test, tip 42 was biased positive 1 volt relative to substrate 41 for 10 milliseconds and caused atom 43 to be transferred from the substrate to the tip as shown at T. Following the transfer, the voltage was reduced to between 10 and 50 millivolts, the voltage 45 (FIG. 5) used to image the surface 40. Tip 42 carrying the Xe atom 43 at or near its apex was then raised from position T to position U, and thereafter moved laterally to position V at a new location. Atom 43 was transferred back to surface 40 by moving tip 42 to position W within a distance e from the surface, which may or may not be the same as distance d. A voltage pulse 46 of appropriate magnitude and duration, but a polarity (see FIG. 5) opposite that used to transfer the Xe atom 43 to the tip 42 ($-1$ volt for 10 milliseconds), was then applied between the tip and substrate 41 and caused the Xe atom to transfer from the tip to the surface as shown at X; whereupon tip 42 was withdrawn to position Y.

It will be understood that the atom 43 may be transferred to a different location on the same substrate 41, as above described, or to a location on a different substrate. Also, tip 42 may be used to image the surface 40 while moving to the new location on the same or a different substrate. Moreover, the voltage pulses may not necessarily be of opposing polarities; in some applications, the transfers from and to the STM tip may be effected by, for example, changes in pulse magnitude of the same polarity. Also, while tip 42 is preferably retracted to position U and moved therefrom to position V, it may, if preferred, be moved laterally from position T to position W if the substrate surface 40 is smooth enough.

The mechanism by which atom 43 is transferred is not currently understood. Although a voltage pulse was applied to transfer the Xe atom, at this time it is not known whether the critical parameter which determines whether or not the atom moves is the voltage, the electric field, the current, or as yet some unanticipated cause.

V

The "dragging" method of Section I and "carrying" methods described in Sections III and IV may be used to reposition and attach an atom to one or more other atoms 15 (FIG. 1) of the same or different type at the desired new location. A molecular compound may be synthesized, for example, by repositioning a C atom to attach to one or more H atoms. The atom being moved should be positioned in sufficiently close proximity to another atom to create a desired structure, typically to within a distance comparable to an interatomic bond length. This process may be used to fabricate structures which, by virtue of their small size, exhibit novel behavior or useful properties derived from the nonclassical or quantum mechanical behavior of such small structures.

The "carrying" method is readily adaptable to constructing on a surface three-dimensional objects (i.e., an assembly of atoms 50 of the same or different types that protrude more than one atomic layer beyond surface 51, such as shown in FIG. 6) because the atom to be added to the three-dimensional object under construction may simply be carried up to its new height by the STM tip in the same way a crane is employed to construct a tall building. The "dragging" process may also allow building in three dimensions; however, it will require that atoms be slid up and over other atoms on the surface.

The methods in Sections I, III, and IV may also be used to cleave or disassemble a multi-atom structure by selectively removing atoms from the structure.

Alternatively, these methods may be used to change the state of an atom or a multi-atom structure. This may be useful for changing the chemical reactivity of the atom or multi-atom structure, or to store information according to the particular state of the atom or multi-atom structure. For example, a diatomic molecule, such as oxygen, can adhere to a surface in one of three possible ways or states: (1) a molecular physisorbed state in which the two oxygen atoms are bound to each other but very weakly to a substrate surface; (2) a molecular chemisorbed state in which the oxygen atoms are still bound together but more strongly bonded to the surface; and (3) a dissociated chemisorbed state in which the oxygen molecule is broken into separate oxygen atoms, both of which are even more strongly bound to the surface. States (1) and (2) are stable at low temperatures (e.g., below 150° K.) if left unperturbed.

Finally, after the repositioning step, one or more of the repositioned atoms may be subjected to a catalyzing agent (such as light, voltage, current, etc.) for causing a chemical reaction that results in a desired multi-atom structure.

It is to be noted that the prior art does not teach or suggest repositioning a selected atom by use of an STM, or the fabrication, disassembly, synthesis, or cleavage of a multi-atom structure.

While the invention has been particularly shown and described with reference to preferred embodiments thereof, it will be understood by those skilled in the art that various changes in form and details may be made therein without departing from the spirit and scope of the invention. Accordingly, the method and structure herein disclosed are to be considered merely as illustrative and the invention is to be limited only as specified in the claims.

I claim:

1. A method of fabricating a desired multi-atom structure on a substrate, comprising the steps of:
   providing a plurality of atoms of the same type; and
   using an STM, repositioning said atoms on the substrate to create the structure.

2. A multi-atom structure fabricated by the method of claim 1.

3. A method of synthesizing a molecule, comprising the steps of:
   providing one atom; and
   using an STM, repositioning said one atom proximate to one or more other atoms of the same type to create the synthesized molecule.

4. A method for repositioning adsorbate atoms on a substrate surface, comprising the steps of:
   while the tip of an STM is positioned proximate a selectable group of atoms to be moved, applying a voltage between the tip and substrate to increase the attraction between the tip and one or more atoms of said group; and
   while the group of atoms remains bound to the surface, moving the tip laterally to drag said group of atoms to a desired position on the surface.

5. A method for repositioning atoms on a substrate surface, comprising the steps of:
   while the tip of an STM is positioned within an effective distance from a selectable group of atoms to be moved, applying a voltage pulse between the tip and atom group for attracting said group of atoms to the tip;
   moving the tip laterally to shift the group of atoms concurrently to a desired position with respect to the surface; and
   while the tip is within said distance, applying a voltage pulse between the tip and substrate for causing said group of atoms to become repositioned on said surface.

6. The method of claim 5, wherein said group is a three-dimensional cluster of atoms that is transferred to the surface.

7. A method for repositioning an adsorbate atom on a substrate surface, comprising the steps of:
   while the tip of an STM is positioned proximate the atom to be moved, applying a voltage pulse between the tip and substrate to change the state of the atom; and
   while the atom in its changed state remains bound to the surface, moving the tip laterally to drag said atom to a desired position on the surface.

8. The method of claim 7, wherein during the moving step, the atom in its changed state is associated with at least one other atom to create a desired structure.

9. The method of claim 7, including the step of:
   applying a voltage pulse between the tip and substrate to again change the state of said atom.

10. The method of claim 7, including the step of:
    providing at least one other atom of the same or a different type bound to the surface and to which the first-mentioned atom is attached when in said desired position.

11. A method of changing the state of a molecule, comprising the steps of:
    providing on a substrate an adsorbate molecule capable of assuming a plurality of different states;
    while the molecule is in one of said states and the tip of an STM is positioned within a predetermined effective distance from said molecule, applying a voltage pulse between said tip and substrate to alter the attraction between the tip and at least one atom of the molecule; and
    repositioning said at least one atom for changing the state of the molecule from its said one state to another of its said plurality of states.

12. The method of claim 11, including the step of:
    while the tip is positioned within said effective distance from said molecule, applying a voltage pulse between said tip and substrate; and
    repositioning the same or a different at least one atom to again change the state of the molecule.

13. A method of fabricating a desired multi-atom structure on a substrate, comprising the steps of:
    providing a plurality of atoms of the same type in disparate locations; and
    using an STM, repositioning at least some of said atoms in sufficiently close proximity to each other on the substrate to create the structure.

14. A method of fabricating a desired multi-atom structure on a substrate, comprising the steps of:
    providing a plurality of atoms in disparate locations;
    using an STM, repositioning at least some of said atoms in sufficiently close proximity to each other on the substrate to create the structure;
    while the tip is within an effective distance from a selected atom to be repositioned, applying a voltage/current pulse between the tip and selected atom to transfer the latter to the tip;
    moving the tip laterally for moving the selected atom to a desired position; and
    while the tip is within said effective distance of said substrate, applying a voltage/current pulse between the tip and substrate to transfer the selected atom to the substrate in a desired spatial relationship with respect to another of said plurality of atoms.

15. The method of claim 14, wherein during the repositioning step, at least some of said atoms are positioned over others of said atoms to form a multi-layered three-dimensional structure.

16. A multi-layered structure made by the method of claim 15.

17. The method of modifying a multi-atom structure comprising the step of:
    using an STM, repositioning at least one atom of the structure.

18. A multi-atom structure modified by the method of claim 17.

19. A method of modifying a molecule, comprising the steps of:
    (a) positioning the tip of an STM within an effective distance from a surface that supports an atom that is to be repositioned to modify the molecule;
    (b) transferring the atom to the tip while the tip is so positioned;
    (c) repositioning the tip proximate to the molecule;
    (d) transferring the atom from the tip to the molecule; and
    (e) repeating steps (a), (b), (c), and (d) for transferring atoms selectively as necessary to complete modification of the molecule.

20. A method of repositioning an atom using an STM having a tip, comprising the steps of:
    providing a substrate to which the atom is bound;
    targeting the atom on the substrate with the tip;
    with the tip in close proximity to the atom, applying a voltage/current pulse to cause the atom to become bound to the tip and remain bound to the tip when the tip is withdrawn from the substrate;
    withdrawing the tip from the substrate;
    moving the tip generally laterally to a desired position above said or another substrate;
    lowering the tip at said position; and
    with the tip in close proximity to the selected substrate at the desired location, applying a voltage/current pulse to cause the atom to be transferred to the selected substrate at the desired location and remain bound thereto upon withdrawal of the tip.

21. A multi-atom structure comprising a substrate having a surface with an area that has a predetermined atomic pattern formed by atoms selectively repositioned on the surface.

22. The structure of claim 21, wherein the atoms are selectively positioned and repositioned by an STM.

23. A multi-atom, three-dimensional structure comprising a substrate having a surface with an area that has a three-dimensional atomic pattern formed by atoms selectively repositioned on the surface.

24. The structure of claim 23, wherein the atoms are selectively positioned and repositioned by an STM.

25. A multilayered, three-dimensional structure comprising a substrate having a surface with at least one atom adsorbed thereon, and at least one different atom superimposed on at least one of the first-mentioned atoms to create the three-dimensional structure.

26. A method of repositioning atoms to synthesize a molecule, comprising the steps of:
    providing at least one adsorbate atom of one type; and
    using an STM, repositioning each such atom in physical contact with an atom of the same type to create the synthesized molecule.

* * * * *

UNITED STATES PATENT AND TRADEMARK OFFICE
CERTIFICATE OF CORRECTION

PATENT NO. : 5,144,148
DATED : Sep. 1, 1992
INVENTOR(S) : EIGLER

It is certified that error appears in the above-identified patent and that said Letters Patent is hereby corrected as shown below:

On title page, item [54] and col. 1, lines 1-3,

Title should read as follows:

--PROCESS AND STRUCTURE WHEREIN ATOMS ARE REPOSITIONED ON A SURFACE USING A SCANNING TUNNELING MICROSCOPE--.

Column 3, line 7: "top" should be "tip"

Signed and Sealed this

Fourteenth Day of September, 1993

Attest:

BRUCE LEHMAN

Attesting Officer

Commissioner of Patents and Trademarks